US012765766B2

(12) United States Patent
Shiba et al.

(10) Patent No.: US 12,765,766 B2
(45) Date of Patent: Oct. 20, 2026

(54) OCT DEVICE, AND STORAGE MEDIUM FOR STORING OCT DATA PROCESSING PROGRAM

(71) Applicant: NIDEK CO., LTD., Gamagori (JP)

(72) Inventors: Ryosuke Shiba, Gamagori (JP); Hirofumi Yogo, Gamagori (JP); Yukihiro Higuchi, Gamagori (JP)

(73) Assignee: NIDEK CO., LTD.

( * ) Notice: Subject to any disclaimer, the term of this patent is extended or adjusted under 35 U.S.C. 154(b) by 287 days.

(21) Appl. No.: 18/477,084

(22) Filed: Sep. 28, 2023

(65) Prior Publication Data

US 2024/0108215 A1 Apr. 4, 2024

(30) Foreign Application Priority Data

Sep. 30, 2022 (JP) ................................ 2022-158459

(51) Int. Cl.

| | |
|---|---|
| ***A61B 3/10*** | (2006.01) |
| ***A61B 3/14*** | (2006.01) |
| ***G06T 5/00*** | (2024.01) |
| ***G06T 5/70*** | (2024.01) |
| ***G06T 7/00*** | (2017.01) |

(52) U.S. Cl.

CPC ................ *A61B 3/102* (2013.01); *A61B 3/14* (2013.01); *G06T 5/70* (2024.01); *G06T 7/0012* (2013.01); *G06T 2207/30041* (2013.01)

(58) Field of Classification Search

CPC ......... A61B 3/0025; A61B 3/102; A61B 3/14; G06T 5/70; G06T 7/0012; G06T 2207/30041

See application file for complete search history.

(56) References Cited

U.S. PATENT DOCUMENTS

2013/0208968 A1 8/2013 Hanebuchi et al.

FOREIGN PATENT DOCUMENTS

| | | | |
|---|---|---|---|
| JP | 2013-156229 | A | 8/2013 |
| JP | 2021-041141 | A | 3/2021 |
| WO | WO 2022-106516 | A | 5/2022 |

*Primary Examiner* — Jack Dinh

(74) *Attorney, Agent, or Firm* — Yusuke Hirai; Best Mode IP Law, PLLC

(57) ABSTRACT

An OCT device includes a controller configured to: acquire OCT data of a tissue of a subject in a depth direction that is generated by processing interference signal detected by a light receiving element; and perform a correction process to reduce an effect by a noise floor in the OCT data using a plurality of correction amounts each of which is set in accordance with depth at a corresponding data acquisition position. Strength of the noise floor varies depending on the depth of the data acquisition position.

11 Claims, 8 Drawing Sheets

OCT DEVICE, AND STORAGE MEDIUM FOR STORING OCT DATA PROCESSING PROGRAM

CROSS REFERENCE TO RELATED APPLICATION

This application claims the benefit of priority from Japanese Patent Application No. 2022-158459 filed on Sep. 30, 2022. The entire disclosure of the above application is incorporated herein by reference.

TECHNICAL FIELD

This disclosure relates to a method and an OCT (Optical Coherence Tomography) device that obtain tissue data of a subject based on the principles of OCT, and a storage medium storing an OCT data processing program designed to process data obtained based on the principles of the OCT.

BACKGROUND

An OCT device directs measurement light split from OCT light towards the subject while guiding reference light toward a reference optical system. The OCT device acquires OCT data based on the interference signal obtained by combining the reflected measurement light reflected from the subject (e.g., a subject eye) and the reference light. For instance, the OCT device is used to obtain cross-sectional images of biological tissues such as an eyeball or skin.

Various techniques have been proposed to mitigate negative effects by noises in the OCT data of the subject (e.g., a subject eye). For example, a technique has been proposed to eliminate FPN (Fix Pattern Noise) which appears in a part of the cross-sectional image in its depth direction.

SUMMARY

One of the noises present in OCT data is a noise floor, which generates over the entire OCT data due to components of the OCT device itself (hereinafter, may be referred to as a "background noise"). Traditionally, since the range of the subject in the depth direction where OCT data was acquired was small, negative effects by the noise floor, whose intensity changes depending on data acquisition depths, were not noticed. However, in recent years, due to advancements of, e.g., wide-angle imaging techniques, deeper-range OCT data can be obtained. For OCT data acquired on a broader depth range, the negative effects by the noise floor whose intensity varies depending on depths tend to clearly appear. Moreover, by processing data obtained by an OCT device, the noise floor unintentionally increases. Therefore, a technology to appropriately reduce the negative effects by the noise floor in OCT data has been desired.

One of objectives of the present disclosure is to provide a method, an OCT device, and a storage medium storing an OCT data processing program that are configured to appropriately reduce negative effects due to the noise floor in the OCT data.

In a first aspect of the present disclosure, a method includes: acquiring OCT data of a tissue of a subject eye in a depth direction that is generated by processing an interference signal generated from measurement light reflected by the tissue and reference light that are split by a light splitting element; performing a correction process to reduce an effect by a noise floor in the OCT data using a plurality of correction amounts each of which is set in accordance with depth at a corresponding data acquisition position, wherein strength of the noise floor varies depending on the depth; generating an image data of the tissue based on the OCT data on which the correction process was performed in accordance with the depth at the corresponding data acquisition position; and acquiring a high-quality image data by inputting the image data into a mathematical model that has been trained by a machine learning algorithm to output improved-quality image data from input image data.

In a second aspect of the present disclosure, an OCT device includes: an OCT light source; a light splitting element that is configured to split light emitted from the OCT light source into measurement light and reference light; an optical system that is configured to guide the measurement light split by the splitting light element toward a tissue of a subject eye; a light receiving element that is configured to detect an interference signal generated from the measurement light reflected by the tissue and the reference light split by the light splitting element; and a controller configured to: acquire OCT data of the tissue in a depth direction that is generated by processing the interference signal detected by the light receiving element; and perform a correction process to reduce an effect by a noise floor in the OCT data using a plurality of correction amounts each of which is set in accordance with depth at a corresponding data acquisition position. Strength of the noise floor varies depending on the depth of the corresponding data acquisition position.

In a third aspect of the present disclosure, a non-transitory, computer readable, storage medium stores an OCT data processing program that is executed by a controller of an OCT data processing device that is configured to process data acquired by an OCT device. The program, when executed by the controller, causes the controller to perform: acquiring OCT data of a tissue of a subject eye in a depth direction that is generated by processing an interference signal generated from measurement light reflected by the tissue and reference light that are split by a light splitting element; and performing a correction process to reduce an effect by a noise floor in the OCT data using a plurality of correction amounts each of which is set in accordance with depth at a corresponding data acquisition position. Strength of the noise floor varies depending on the depth at the corresponding data acquisition position.

According to the above-described aspects, the negative effects by the noise floor in the OCT data can be appropriately reduced.

DESCRIPTION OF EMBODIMENTS

Overview

Figure 1:
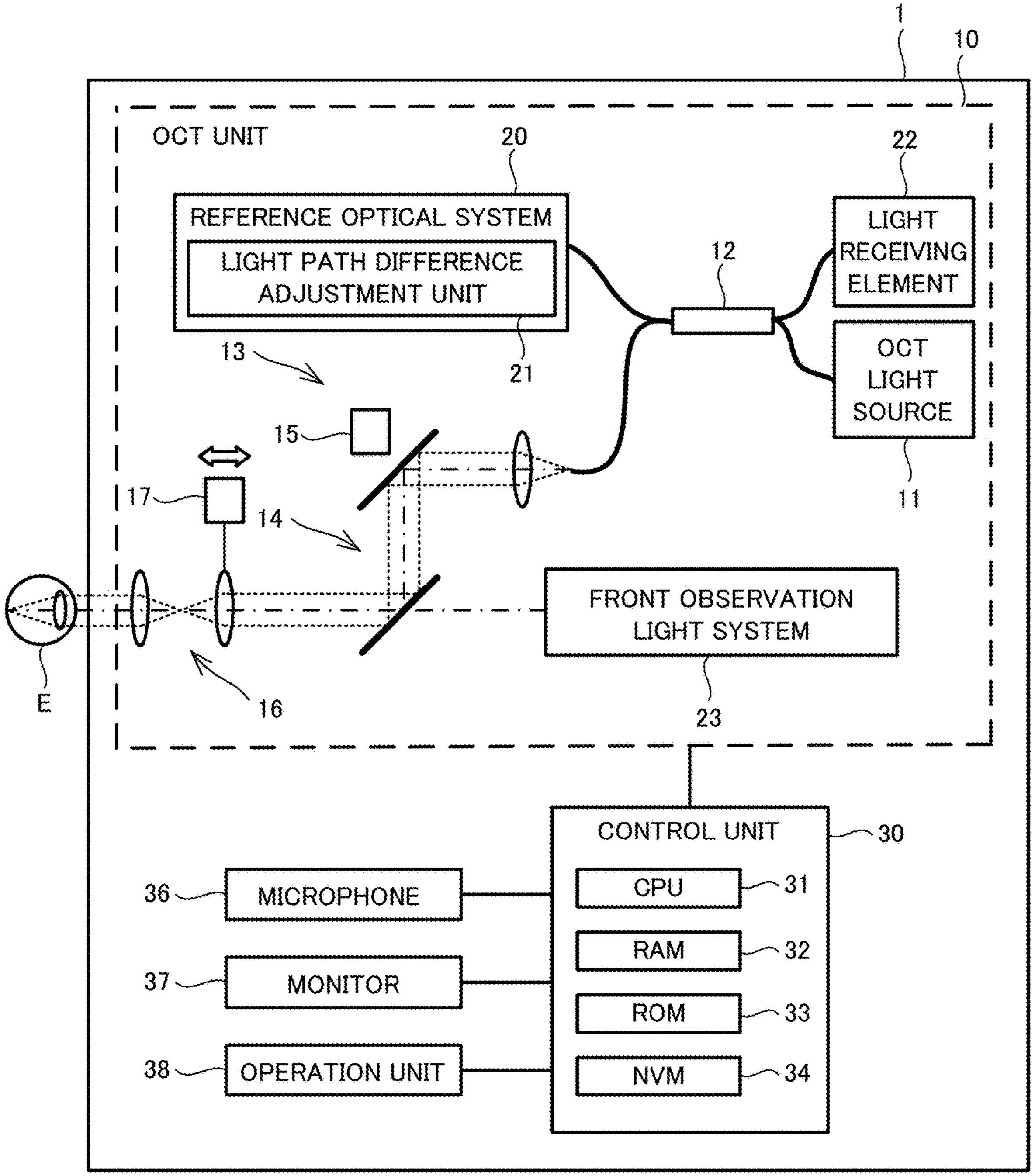
FIG. 1 is a block diagram showing a schematic configuration of an OCT device.

An OCT device in the present disclosure includes an OCT light source, a light splitting element, an optical system, a light receiving element, and a control unit. The OCT light source emits OCT light. The light splitting element divides the light emitted from the OCT light source into measurement light and reference light. The light receiving element detects an interference signal of the measurement light reflected by the tissue and the reference light split by the light splitting element. The control unit controls the OCT device and executes an OCT data acquisition step and a correction step. In the OCT data acquisition step, the control unit acquires OCT data in the depth direction of the tissue, which is generated by processing the interference signal detected by the light receiving element. In the correction step, the control unit performs a correction process to reduce effects by noise floor, whose intensity changes depending on the depth of the data acquisition position, using correction amounts each corresponding to depth at the corresponding data acquisition position in the OCT data.

It was found that the noise floor that generates across the OCT data due to the OCT device itself varies in intensity depending on the depths at the data acquisition positions. Especially in recent years, developed technologies make it possible to acquire OCT data over a wide range of the tissue in the depth direction, Therefore, variations in the noise floor depending on the depths at the data acquisition positions tend to increase. When the influence due to the noise floor variations increases, a luminance difference in noise between a deep region and a shallow region arises, resulting in a decrease in the image quality of the image generated based on the OCT data. Moreover, the accuracy of various processes executed on the image generated based on the OCT data (for example, an image improvement process using an algorithm of machine learning or image processing, or a segmentation process identifying a specific part in the image, such as layers or boundaries) would also decrease. Since conventional algorithms assumed that the luminance of the noise floor is constant regardless of the depths, it is difficult for conventional techniques to appropriately suppress the negative effects by the noise floor.

In contrast, the OCT device (or an OCT data processing device) according to the present disclosure executes the correction process to suppress negative effects by the noise floor in the OCT data (i.e., the noise floor whose intensity varies depending on the depths at the data acquisition positions) using correction amounts each corresponding to the depth at the corresponding data acquisition position. As a result, the quality of the data acquired by the OCT device can be appropriately improved.

In the present disclosure, a complex OCT (Optical Coherence Tomography) signal is obtained by performing a Fourier transform on the spectral intensity of the interference signal acquired by the light receiving element. By processing the complex OCT signal (e.g., calculating the absolute value of the amplitude in the complex OCT signal), OCT data in the depth direction at the data acquisition position (hereinafter, referred to as "RAW data") is acquired. In this disclosure, by correcting the RAW data obtained through the processing of the complex OCT signal using depth-dependent correction amounts, the negative effects by the noise floor can be reduced. However, the details of the correction process may be modified. For example, the effects by the noise floor may be suppressed by performing the correction process on the complex OCT signal. Furthermore, by applying a depth-dependent correction amount to a parameter (e.g., a threshold value) used during processing of the OCT data (e.g., the quality improvement process and the segmentation process), the effects by the noise floor may also be reduced.

In this disclosure, the OCT device that acquires the OCT data functions as the OCT data processing device that performs the correction process. Therefore, the OCT device can acquire data based on the principles of OCT, and then appropriately process the acquired data. However, the device functioning as the OCT data processing device is not necessarily limited to the OCT device. For example, a personal computer (hereinafter, referred to as a "PC") capable of acquiring data collected by the OCT device may serve as an OCT data processing device. Additionally, multiple devices (e.g., an OCT device and a PC) may cooperate to perform the correction process and may function as the OCT data processing device.

The OCT device may also be equipped with a light scanning unit. This light scanning unit scans the tissue with the measurement light, which is emitted onto the tissue by the optical system, in a two-dimensional direction intersecting the optical axis. The OCT data may be acquired by scanning the tissue with the spot of the measurement light in a two-dimensional direction within a measurement area by the light scanning unit. However, the configuration of the OCT device may be modified. For instance, the optical system of the OCT device may simultaneously emit the measurement light onto a two-dimensional region of the tissue of the specimen. In this case, the light receiving element may be a two-dimensional light receiving element that detects interference signals for a two-dimensional region on the tissue. In other words, the OCT device may acquire OCT data based on the principle of full-field OCT (FF-OCT). Also, the OCT device may emit the measurement light along an emission line extending in a one-dimensional direction onto the tissue while scanning the tissue with the measurement light in a direction intersecting the emission line. In this case, the light receiving element may be either a one-dimensional light receiving element (e.g., a line sensor) or a two-dimensional light receiving element. In other words, the OCT device may acquire a cross-sectional image based on the principle of line-field OCT (LF-OCT).

The control unit may perform the correction process using a correction amount, which is a product of the data acquisition depth and a correction coefficient based on a variation amount of the noise floor per unit change in depth. According to new findings obtained by inventors of the present disclosure, the noise floor of OCT data tends to attenuate (gradually decrease) in rough proportion to the depths at the data acquisition positions. Therefore, by using a value obtained by multiplying the data acquisition depth by the correction coefficient as a depth-dependent correction amount, the negative effects by the noise floor, whose intensity varies depending on the depths, can be appropriately reduced. Moreover, the correction value for each depth is calculated simply by multiplying the correction coefficient by the depth. Consequently, the influence due to the noise floor can be reduced without decreasing processing speed and without consuming excessive memory capacity. The correction coefficient is one example of a correction parameter used to determine the correction value for the OCT data depending on the depths.

However, details of the correction process may be modified. For instance, the control unit may acquire correction amount data, where each of correction amounts is defined for the corresponding depth, as a correction parameter. The control unit may perform the correction process using the correction amounts defined for the corresponding depths by the correction amount data. In this case, even if the OCT device has the noise floor that does not vary proportionally with depths, the influence due to the noise floor can be suitably reduced. Additionally, the control unit may perform curve fitting to the attenuation of the noise floor with depths and acquire a depth-dependent correction amount based on the obtained approximate curve. In this case, the control unit may acquire the depth-dependent correction amount using, as the correction parameter, a function of depth (such as a quadratic function or a higher-order function) that corresponds to the obtained approximate curve.

Furthermore, when acquiring the depth-dependent correction amount using a function, the control unit may also use the function's intercept to acquire the depth-dependent correction amount. In this case, the influence due to the noise floor is more likely to be reduced regardless of the sensitivity of the OCT, among other factors.

The correction parameter (e.g., a correction coefficient) based on the variation in signal intensity according to depths at the data acquisition positions in data obtained by the OCT device actually performing the imaging operation may be particularly set for the OCT device. The intensity and variations of the noise floor are influenced by various factors such as the OCT light source and the light receiving element. Thus, when multiple OCT devices with the same configuration are manufactured, differences in the noise floor's intensity and variations would arise among the OCT devices. Therefore, by setting the correction parameter based on the data that is actually acquired by the OCT device, the influence due to the noise floor can be adequately reduced regardless of the existence of the device characteristic variation.

Alternatively, instead of using the correction coefficient, correction data defined for each of depths or a function to acquire the correction amount may be used as the correction parameter. Even in these cases, the correction parameter may be particularly set for the OCT device based on data acquired by the OCT device itself that performs an imaging operation. This means that correction values in the correction process based on the depths at the data acquisition positions can be set based on magnitude of the signal intensity in the data obtained by the OCT device itself that performs the imaging operation.

However, the correction parameter (e.g., a correction coefficient) may be a fixed value commonly used for multiple OCT devices. Even in this scenario, by performing the correction process based on the depth at the data acquisition position, the influence by the noise floor can be adequately reduced.

The correction parameter (e.g., the correction coefficient) may be preset for the OCT device based on data acquired from past imaging operations performed by the OCT device. According to new findings by the inventor of the present disclosure, while the noise floor in OCT data is easily influenced by various factors such as the OCT light source and the light receiving element, the noise floor is found to be less affected by an imaging environment such as temperature. Thus, by particularly customizing the correction parameters for the OCT device based on the past acquired data, there is no need to set the correction parameter every time the OCT data is acquired. This allows the influence by the noise floor to be easily and adequately reduced with a simple process.

The timing for setting the correction parameter may be chosen appropriately. For example, after the OCT device is manufactured but before shipped, the correction parameter may be set based on data acquired by the OCT device itself by performing an imaging operation. In this case, the control unit of the OCT device may calculate and set the correction parameter. Alternatively, a previously calculated correction parameter may be stored in the memory device of the OCT device. Also, during maintenance or parts replacement for the OCT device, the correction parameter may be set.

Alternatively, in place of a correction coefficient, depth-specific correction data or function may be used as a correction parameter. Even in these cases, there is no need to set correction parameters every time OCT data is acquired.

The control unit may set a correction parameter (e.g., a correction coefficient) every time the imaging operation is performed based either on the data itself acquired through the imaging operation or data acquired before and after performing the imaging operation. By setting the correction parameter every time the imaging operation is performed, the influence by the noise floor, which may be affected by an imaging environment, is more likely to be adequately reduced.

The correction parameters (e.g., a correction coefficient) may be set based on the variation in signal intensity according to depths at the data acquisition positions in dark data which has no signal increase due to the reflected light of the measurement light. In the dark data, the signal caused by the reflected light reflected from an imaging target is less likely to increase. Thus, only signals caused by the noise floor is likely to appear in the dark data. Thus, by setting correction parameter based on the dark data, the correction parameter suited to the actual noise floor can be set with higher accuracy.

The correction parameters may be particularly preset for the OCT device based on the dark data acquired from past imaging operations performed by the OCT device itself. In this case, the influence by the noise floor is more likely to be easily and adequately reduced with highly accurate correction parameters.

Furthermore, the control unit may set correction parameters based on the dark data obtained before and after performing each imaging operation. In this case, the influence by the imaging environment and the like on the noise floor can be also reduced, making it easier to accurately reduce the negative effects by the noise floor.

The specific method for setting the correction coefficient based on the dark data may be chosen as appropriate. For instance, an approximate straight line for the signal strength at each depth in the dark data may be calculated, and the correction coefficient may be set based on the slope of the determined approximate straight line. This approximate line may, for example, be a regression line determined by the least squares method. It is also possible to perform the correction process based on an approximate curve for the signal strength at each depth in the dark data, depending on the depths at the data acquisition positions. Additionally, an intercept may be calculated from the signal strength at each depth in the dark data, and the calculated intercept may also be used to obtain the correction amount based on the depth.

Even when correction amount data or functions that are defined for corresponding depths are used as correction parameters instead of using the correction coefficient, the correction parameters may be set based on the dark data. In such cases, correction parameters suited to the actual noise floor are likely to be set with high accuracy.

Instead of using the dark data, the correction parameters may be set based on data obtained under a normal condition where the reflected light of the measurement light is allowed to enter the light receiving element (e.g., OCT data obtained by actually imaging the tissue of the subject eye). In this case, for example, a principal component analysis may be performed on the signal strength at each depth in the obtained OCT data, and the correction parameters (e.g., a correction coefficient) may be set based on the slope of the obtained first principal component. For instance, such a principal component analysis may be applied when setting the correction coefficient based on the OCT data itself obtained by performing the imaging operation. Additionally, in images generated from OCT data where the influence due to the noise floor is reduced with high accuracy, the standard deviation (variance) and entropy of the image tend to be small. Therefore, correction parameters may be set by searching for a correction parameter that causes the evaluation value of the standard deviation (variance) or entropy of the image generated from the OCT data to decrease.

The control unit, depending on the number of interference signals per unit time acquired by the light-receiving element when the OCT data is obtained, may change the correction amount (e.g., the aforementioned correction coefficient, correction amount data, function, or other correction parameters) according to the depths at the data acquisition positions. According to a new insight obtained by the inventor of the present disclosure, when the number of interference signals acquired per unit time by the light receiving element increases (i.e., when the exposure time of the light receiving element is shortened), both the signal strength of the noise floor and the change in the strength of the noise floor with depths increase. Therefore, by changing the correction amount based on depth in the correction process depending on the number of interference signals acquired per unit time by the light receiving element, the negative effects by the noise floor can be accurately reduced.

Additionally, the OCT device may further include a light scanning unit that scans the tissue with the measurement light. The control unit may change the correction amount based on the depths at the data acquisition positions depending on the scanning speed of the measurement light by the light scanning unit and the number of interference signals acquired per unit time by the light receiving element (collectively referred to as a "scanning rate"). In this case, the negative effects by the noise floor can be accurately reduced depending on the scanning rate.

Changing the correction amount based on depth depending on the exposure time or the scanning rate is particularly effective when correcting the OCT data based on the preset correction parameters (e.g., when correction parameters are particularly preset for the OCT device based on previously obtained data).

The control unit may generate image data of the tissue (that is, image data with a corrected noise floor) based on OCT data on which the correction process was performed depending on the depths at the data acquisition locations. The control unit can obtain improved high-quality image data by inputting the corrected noise floor image data into a mathematical model trained by a machine learning algorithm to output data of an improved quality image from the input image data. If image data is input without performing the noise floor correction into the mathematical model, often, a high-quality image with reduced effects by the noise floor is less likely to be acquired. For instance, when inputting image data into the mathematical model, high-luminance areas that would not appear if there is no noise floor may be generated in the image output by the model. Specifically, if image data captured by an OCT device with minimal noise floor influence is used as training data when training the mathematical model, an improved quality image may not be acquired. This is because the image data that was used to train the mathematical model has different distribution from the image data input into the mathematical model to improve its quality. Especially, in deep learning models that utilize batch normalization, since the models use the mean and standard deviation of the training data, decrease in quality due to the data distribution difference tends to occur. However, by inputting corrected noise floor image data into the mathematical model according to the present disclosure, higher-quality image data can be easily obtained.

The control unit may generate sectional image data of the tissue (i.e., data of sectional images with a corrected noise floor) based on the OCT data on which the correction process depending on the depth of the data acquisition position was performed. By inputting the corrected noise floor sectional image data into a mathematical model trained by a machine learning algorithm to output the results of whether at least one of multiple layers included in the input sectional image and the boundaries between the layers is identified, it is possible to obtain segmentation results. Based on the sectional images with reduced noise floor effects, accurate identification results can be easily achieved. Even without utilizing a mathematical model and just using known image processing for segmentation, higher accuracy results can be easily achieved.

The control unit may generate motion contrast images (e.g., OCT angiography images) based on at least two OCT datasets that are obtained at different timings for the same tissue position and subject to the depth-dependent correction process. In this case, high-quality motion contrast images with reduced noise floor effects can be easily generated.

The control unit may generate Enface image data based on OCT data that is subject to the depth-dependent correction process. The Enface image data may be, for example, accumulated luminance values in the depth direction (Z-direction) at each of XY-direction positions intersecting the measurement light axis, accumulated values of spectral data at each of XY-direction positions, luminance data in a specific depth direction for each of XY-direction positions, or luminance data at any layer of the retina (e.g., the retinal surface) for each of XY-direction positions. In this case, high-quality Enface images with reduced noise floor effects can be more easily generated.

EMBODIMENTS

Next, a typical embodiment of the present disclosure will be described. As an example, an OCT device 1 of this embodiment is configured to process OCT data of a fundus of a subject eye E. Based on the acquired OCT data, a three-dimensional sectional image and a two-dimensional sectional image are generated. However, even when OCT data of a tissue other than the fundus of the subject eye E (e.g., an anterior part of the subject eye E or other test subjects such as skin, digestive organs, brain, blood vessels (including cardiac vessels), or teeth) is processed, at least some of the techniques disclosed herein may be used. OCT data is data acquired based on the principles of Optical Coherence Tomography (OCT).

In this embodiment, the OCT device 1 serves as an OCT data processing device by executing various processes described below. However, a device that is configured to function as the OCT data processing device is not necessarily limited to the OCT device 1. For example, a PC that is configured to acquire OCT data acquired (captured) by the OCT device 1 may also function as the OCT data processing device.

Referring to FIG. 1, the general configuration of the OCT device 1 according to this embodiment will be described. The OCT device 1 includes an OCT unit 10 and a control unit 30. The OCT unit 10 is equipped with an OCT light source 11, a coupler (optical splitter) 12, a measurement optical system 13, a reference optical system 20, a light receiving element 22, and a front observation optical system 23.

The OCT light source 11 emits light (OCT light) for acquiring OCT data. The coupler 12 divides the OCT light emitted from the OCT light source 11 into measurement light and reference light. Also, the coupler 12 in this embodiment causes the measurement light reflected by the subject (in this embodiment, the retina of the subject eye E) and the reference light generated by the reference optical system 20 to interfere with each other by multiplexing. In other words, the coupler 12 in this embodiment serves as both a light splitting element that splits the OCT light into the measurement light and the reference light and a synthesizing optical element that synthesizes the reflected measurement light and the reference light. It should be noted that it is possible to change the configuration of either or both the light splitting element and the optical synthesizing element. For example, an element other than the coupler (e.g., a circulator, beam splitter, etc.) may be used.

The measurement optical system 13 guides the measurement light divided by the coupler 12 to the subject (the examinee) and returns the measurement light reflected by the subject to the coupler 12. The measurement optical system 13 includes a light scanning unit 14, an illumination optical system 16, and a focus adjustment unit 17. The light scanning unit 14, when driven by the driving unit 15, is configured to emit (deflect) the measurement light in a two-dimensional direction intersecting the optical axis of the measurement light. In this embodiment, two galvanic mirrors capable of deflecting the measurement light in different directions are used as the light scanning unit 14. However, other devices for deflecting light (e.g., a polygon mirror, resonant scanner, acousto-optic element, or the like) may also be used as the light scanning unit 14. The illumination optical system 16 is located downstream of the light scanning unit 14 in the optical path (i.e., on the subject side) and emits the measurement light onto the tissue of the subject. The focus adjustment unit 17 adjusts the focus of the measurement light by moving an optical component (e.g., lens) of the illumination optical system 16 in a direction along the optical axis of the measurement light.

The reference optical system 20 generates the reference light and returns the reference light to the coupler 12. The reference optical system 20 in this embodiment generates the reference light by reflecting the reference light divided by the coupler 12 with a reflection optical system (e.g., a reference mirror). However, the configuration of the reference optical system 20 may also be changed. For instance, the reference optical system 20 may transmit the light incident from the coupler 12 without reflecting the light and return the light to the coupler 12. The reference optical system 20 includes an optical path length difference adjustment unit 21 that adjusts an optical path length difference between the measurement light and the reference light. In this embodiment, the optical path length difference is changed by moving the reference mirror in the optical axis direction. Another member for changing the optical path length difference may also be disposed in the optical path of the measurement optical system 13.

The light receiving element 22 detects interference signals by receiving the interference light generated from the measurement and reference light combined by the coupler 12. In this embodiment, the principle of Fourier Domain OCT is used. In Fourier Domain OCT, the spectral intensity of the interference light (spectral interference signal) is detected by the light receiving element 22, and a complex OCT signal is acquired by performing a Fourier transform on the spectral intensity data. By processing the complex OCT signal (for example, calculating the absolute amplitude value of the complex OCT signal and taking the logarithm of the absolute value), RAW data, which is OCT data in the depth direction at a data acquisition position, is acquired. The RAW data is original OCT data acquired by the OCT device 1 (i.e., data before any correction or other processing described later is made). Examples of Fourier Domain OCT include Spectral-domain-OCT (SD-OCT) and Swept-source-OCT (SS-OCT). Alternatively, Time-domain-OCT (TD-OCT) may also be adopted.

In this embodiment, SD-OCT is used. When the SD-OCT is used, for example, a low-coherence light source (i.e., a broadband light source) is used as the OCT light source 11, and a spectrometer, which spectrally divides the interference light into its frequency components (i.e., wavelength components), is disposed near the light-receiving element 22 in the optical path of the interference light. When the SS-OCT is used, for instance, a wavelength scanning type light source (i.e., a wavelength tunable light source) that rapidly changes its emission wavelength over time is used as the OCT light source 11. In this case, the OCT light source 11 may include a light source, a fiber ring resonator, and a wavelength selection filter. The wavelength selection filter includes, for example, a filter combining a diffraction grating and a polygon mirror, as well as a filter using a Fabry-Perot etalon.

In this embodiment, the OCT data is acquired by emitting (scanning) a measurement light spot within a two-dimensional measurement area by the optical scanning unit 14. However, a different principle for acquiring OCT data may be used. For example, three-dimensional OCT data may be acquired based on the principle of Line-field OCT (hereinafter, referred to as "LF-OCT"). In LF-OCT, measurement light is simultaneously emitted along an emission line extending in one-dimensional direction within the tissue, and the interference light of the reflected measurement light and the reference light is received by a one-dimensional light receiving element (e.g., a line sensor) or a two-dimensional light receiving element. Three-dimensional OCT data is acquired by emitting the measurement light in a direction intersecting the emission line within the two-dimensional measurement area. Additionally, three-dimensional OCT data may also be acquired based on the principle of Full-field OCT (hereinafter, referred to as "FF-OCT"). In FF-OCT, measurement light is emitted onto a two-dimensional measurement area in the tissue, and the interference light between the reflected measurement light and the reference light is received by a two-dimensional light receiving element. In this case, the OCT device 1 may not need to include the optical scanning unit 14.

The front observation optical system 23 is configured to capture real-time front observation images of a subject tissue (in this embodiment, the fundus of the subject eye E). A front observation image in this embodiment is a two-dimensional image of the tissue viewed in a direction (a front side) along the optical axis of the OCT measurement light. In this embodiment, a scanning laser ophthalmoscope (SLO) is used as the front observation optical system 23. However, a configuration other than the SLO (e.g., an infrared camera that irradiates infrared light over a two-dimensional capturing range to capture front images) may also be used as the front observation optical system 23.

The control unit 30 performs various controls of the OCT device 1. The control unit 30 is equipped with a CPU 31, RAM 32, ROM 33, and non-volatile memory (NVM) 34. The CPU 31 acts as a controller for performing various controls. The RAM 32 temporarily stores various information. The ROM 33 stores programs executed by the CPU 31, and various initial values and so on. The NVM 34 is a non-transitory storage medium that is configured to keep stored contents even when power supply is cut off. An OCT data processing program for executing an OCT data process (refer to FIGS. 5-7) may also be stored in the NVM 34.

A microphone 36, a monitor 37, and an operation unit 38 are connected to the control unit 30. The microphone 36 inputs sound. The monitor 37 is one example of a display device that displays various images. The operation unit 38 is operated by users to input various instructions to the OCT device 1. For example, devices such as a mouse, keyboard, touch panel, foot switch, etc., may be used as the operation unit 38. Various instructions may also be input to the OCT device 1 when a sound is inputted into the microphone 36. In this case, the CPU 31 performs voice recognition processing on the input sound to identify the instructions.

In this embodiment, the OCT device 1 integrally includes the OCT unit 10 and the control unit 30 that are built into a single housing. However, the OCT device 1 may also be equipped with several devices with different housings. For example, the OCT device 1 may include an optical device that houses the OCT unit 10, and a PC connected to the optical device via either wireless or wired connection. In this case, the control part of the optical device and the control part of the PC may both function as the control unit 30 of the OCT device 1.

Noise Floor Characteristics

Figure 2:
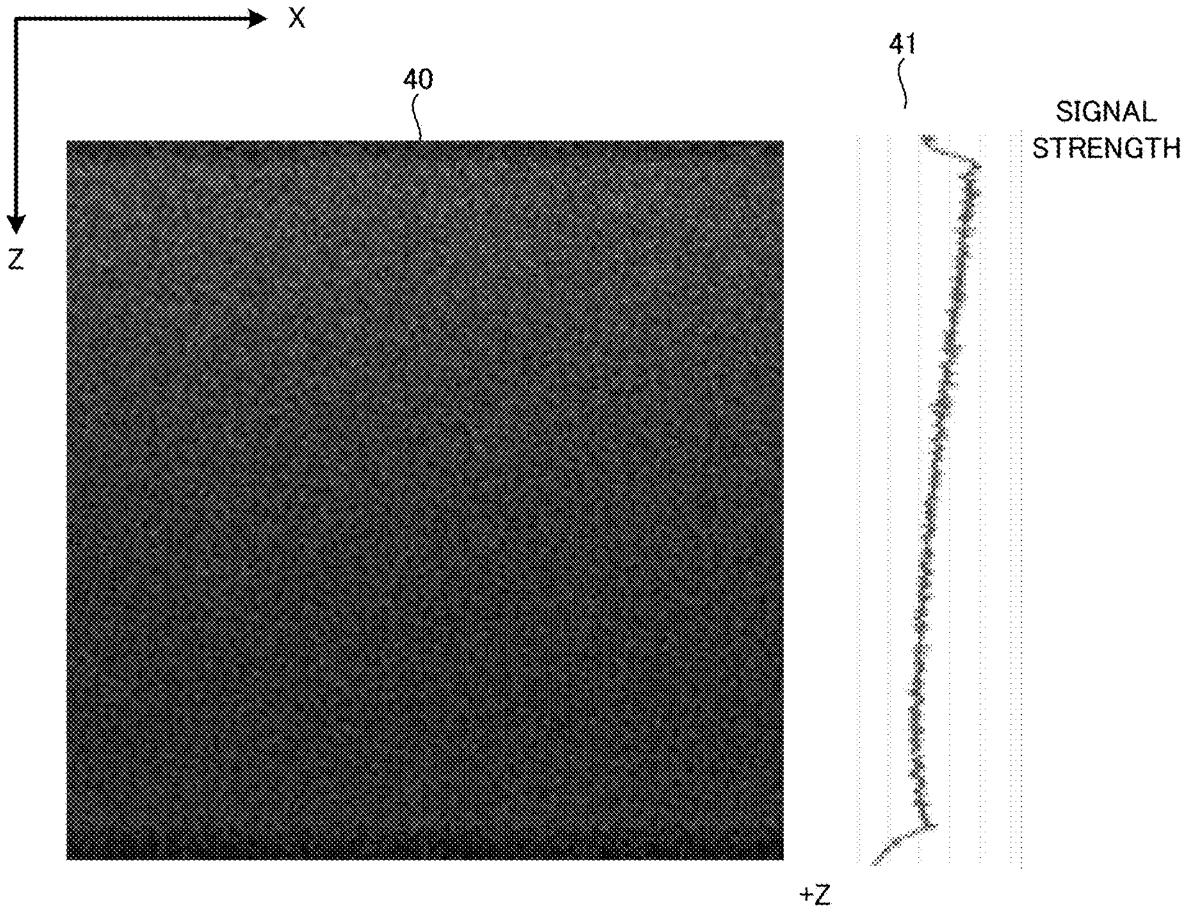
FIG. 2 is a diagram showing a dark image and a luminance graph in the dark image.

Referring to FIG. 2, characteristics of noise floor in the OCT data acquired by the OCT device 1 are described. FIG. 2 illustrates a dark image 40, which is a two-dimensional tomographic image spreading in X-Z direction based on dark data, together with a luminance graph 41 that indicates an average luminance in X-direction of the dark image 40 according to Z-direction. In FIG. 2, Z-direction is the depth direction. As shown in FIG. 2, the lower it goes in the drawing. (i.e., in +Z-direction), the deeper the data acquisition position is. Also, in the luminance graph 41 shown in FIG. 2, the right direction indicates that the signal strength (luminance) of the dark image 40 increases.

The dark data is OCT data where the signal increase due to light reflected by an imaging target (i.e., the subject) does not occur. A specific method to obtain the dark data using the OCT device 1 may be chosen as appropriate. For instance, the dark data may be acquired under the condition where the incidence of the reflected light from the measurement light onto the receiving element 22 is blocked. Specifically, by performing the imaging operation (i.e., OCT data acquisition operation) with the shutter that is disposed in the path of the measurement light to block the measurement light in the OCT device 1, the dark data may be acquired. Alternatively, by scanning with the measurement light that is emitted outside of the path, the dark data may be acquired. Furthermore, the OCT device 1 may acquire the dark data by significantly changing the optical path length so that interference signals (i.e., the interference signals between the reflected measurement light and the interference light) from the imaging target are not obtained. Additionally, the OCT device 1 may obtain the dark data based on data regions that do not contain interference signals after scanning the imaging target with the measurement light. The dark data may be acquired by averaging multiple data points at the same location (e.g., multiple pieces of A-scan data at each of positions). In the dark data, signals due to the reflected light from the imaging target are less likely to increase. Therefore, only signals caused by the noise floor are more likely to appear (generate). Therefore, the noise floor is high likely to cause high pixel brightness in the dark image 40.

As shown in FIG. 2, the strength of the noise floor that generates over the OCT data due to the components of the OCT device varies depending on the depth at the data acquisition position. In detail, the strength of the noise floor attenuates (decreases) as the depth at the data acquisition position increases (i.e., +Z-direction). As illustrated in the brightness graph 41 of FIG. 2, the OCT data noise floor tends to decrease in roughly proportion to the depth of the data acquisition position.

Although the noise floor of the OCT data tends to vary due to the influence of various elements such as the OCT light source 11 and the light receiving element 22, it was newly discovered that the noise floor is less affected by the environment, such as temperature. Furthermore, by increasing the number of interference signals acquired per unit time by the light receiving element 22 (in other words, by shortening the exposure time of the light receiving element 22), both the signal strength of the noise floor and the change in the noise floor's strength according to depth were found to increase. In the processes described below, the OCT data (in this embodiment, RAW data) is corrected in view of at least one of the aforementioned noise floor characteristics.

OCT Data Correction Method

The method for correcting the OCT data (i.e., RAW data) in the embodiments (first to third embodiments) will be described. For comparison, a method of assigning brightness to RAW data is explained first. Initially, an interference signal detected by the light receiving element 22 is processed, and RAW data "I (dB)" is acquired. Subsequently, data that excludes shallow regions susceptible to noise other than the noise floor from the RAW data "I" is designated as data "A". The average brightness "$\mu$" and standard deviation "$\sigma$" in data "A" are calculated. A threshold is defined as "$T=\mu+\sigma$", and data "A" is binarized. In data "A", data with brightness exceeding threshold "T" is considered as foreground data (i.e., a region where an image is shown), and the average brightness "$\mu 2$" and standard deviation "$\sigma 2$" of the foreground data are calculated. Next, offset value "$C=\mu$" and gain value "$G=1/(\mu 2+3.75\sigma 2-C)$" are calculated. Using the calculated gain value "G" and the offset value, brightness of the image is assigned by "$255*(I-C)/G$".

As described above, only a constant offset value "C" is subtracted from the RAW data (or more precisely, from data A which has some regions excluded from the RAW data) irrespective of the depth at the data acquisition position. This means such a conventional method is carried out without considering the change in the noise floor's strength depending on the depth. As a result, there were cases where the influence of the noise floor was not adequately reduced. In contrast, in this embodiment, a correction process is performed on the OCT data according to the depth at the data acquisition position. Therefore, the influence by the noise floor, which changes in strength depending on the data acquisition depth, is appropriately reduced.

As described earlier, the noise floor of the OCT data tends to attenuate in proportion to the depth at the data acquisition position (refer to FIG. 2). Hence, in this embodiment, the OCT device 1 corrects the RAW data by subtracting, from the RAW data (x, z), a value derived by multiplying the depth "z" by a correction coefficient "a" that corresponds to the change in the noise floor per unit change in data acquisition depth. As a result, the influence of the noise floor, which varies in strength according to depth, is appropriately reduced. The correction value "az" for each depth is simply calculated by multiplying the correction coefficient "a" with the depth "z". Therefore, with no significant decrease in processing speed and without reducing memory capacity, the influence by the noise floor is appropriately reduced. Note that the correction coefficient "a" is just one example of a correction parameter to determine the correction value for the OCT data according to depth. Also, in this embodiment, the intercept "b" is calculated from the change in brightness value of the noise floor that attenuates in proportion to depth, and this intercept "b" is also subtracted from the RAW data. As a result, the influence by the noise floor is more likely to be appropriately reduced regardless of OCT sensitivity and other factors.

First Embodiment

Figure 3:
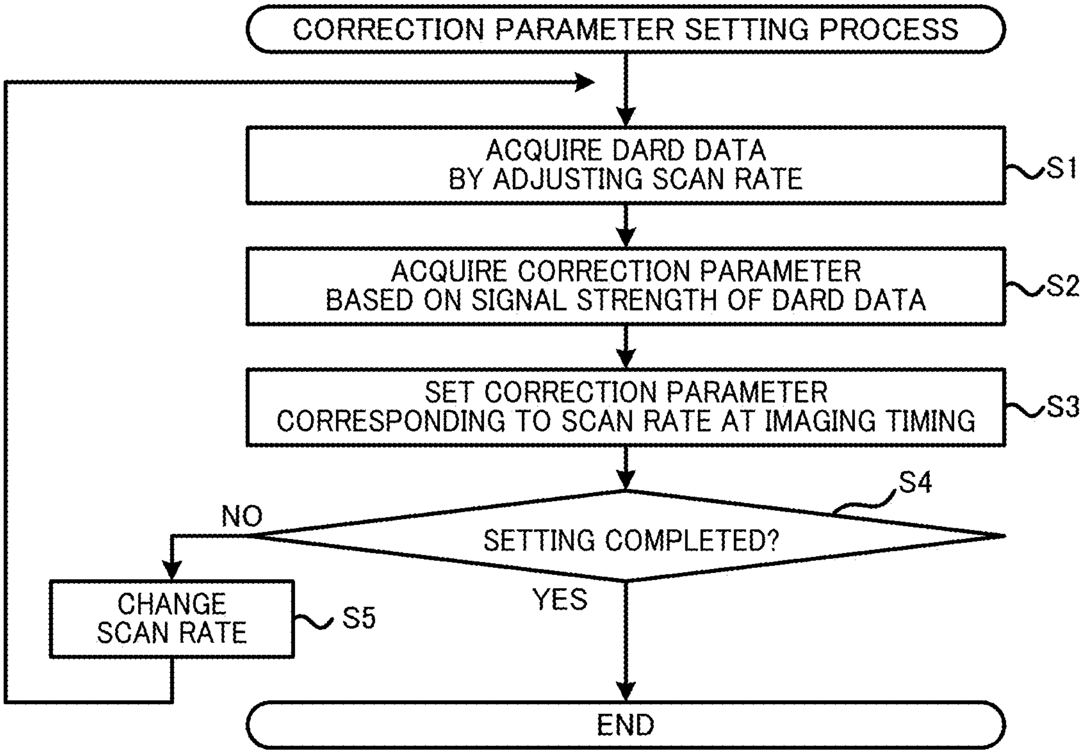
FIG. 3 is a flowchart of a correction parameter setting process executed by the OCT device (i.e., an OCT data processing device) according to a first embodiment.
Figure 4:
FIG. 4 is a diagram showing an approximate straight line derived from the luminance graph shown in FIG. 2.
Figure 5:
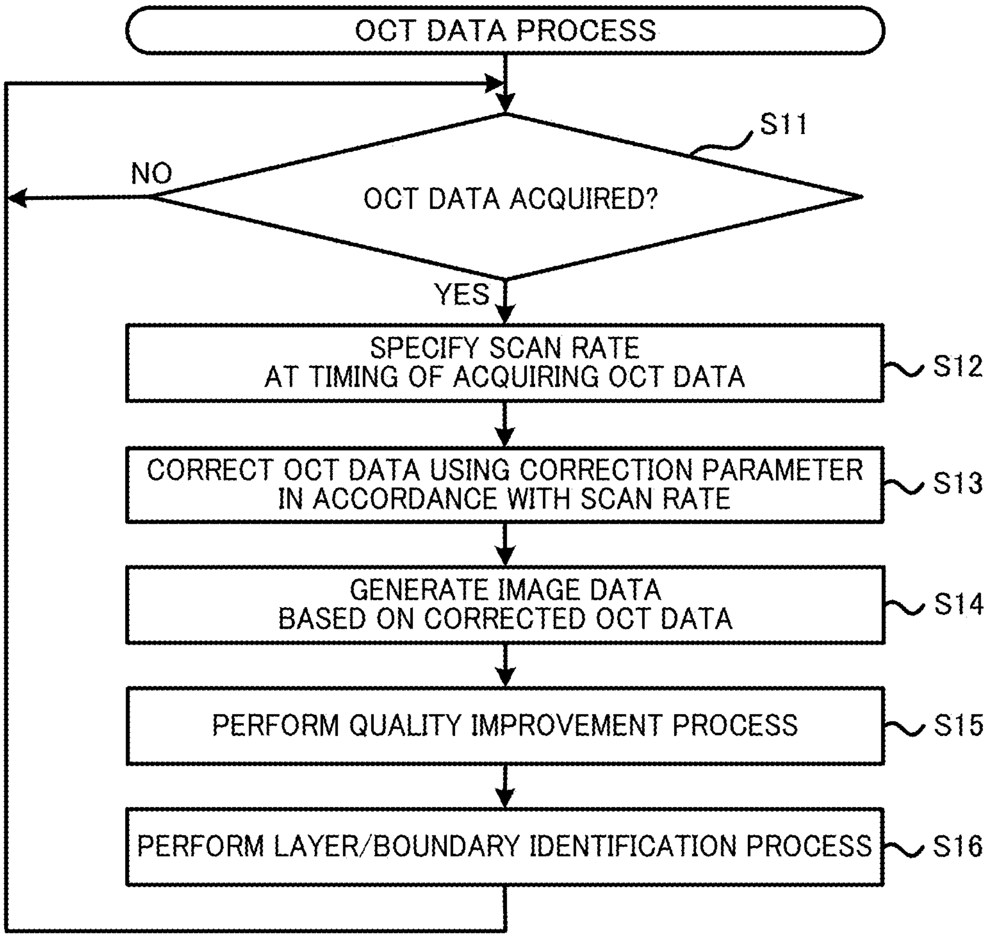
FIG. 5 is a flowchart of an OCT data process executed by the OCT device (i.e., the OCT data processing device) according to the first embodiment.

Referring to FIGS. 3 to 5, the process executed by the OCT device (i.e., the OCT data processing device) 1 in the first embodiment will be described. The OCT device 1 of the first embodiment executes a correction parameter setting process (see FIG. 3) and an OCT data process (see FIG. 5). In the correction parameter setting process, based on the OCT data obtained by the imaging operation performed by the OCT device 1 itself, the correction parameters (in this embodiment, the previously mentioned correction coefficient "a" and the intercept "b") are set for the individual OCT device 1. In the OCT data process, the acquired OCT data (RAW data) is corrected based on the correction parameters to reduce negative effects due to the noise floor.

Referring to FIGS. 3 and 4, the correction parameter setting process will be described. The timing of executing the correction parameter setting process in the first embodiment may be appropriately chosen. For example, the correction parameter setting process may be executed at a timing after manufacturing of the OCT device 1 and before shipping of the OCT device 1. Alternatively, the correction parameter setting process may be executed during the maintenance of the OCT device 1 or when parts of the OCT device 1 are replaced. In this embodiment, the CPU 31 of the OCT device 1 executes the correction parameter setting process shown in FIG. 3 in accordance with the OCT data processing program stored in the NVM 34. However, the correction parameter setting process may be executed by the controller of a device other than the OCT device 1.

As shown in FIG. 3, the CPU 31 captures (photographs) dark data by controlling the optical scanning unit 14 or the like after adjusting a scanning rate (S1). The scanning rate will be described later. As previously mentioned, the dark data is OCT data obtained under a condition where the incidence of the reflected light of the measurement light onto the light receiving element 22 is blocked. In the dark data, signals are less likely to increase due to the reflected light reflected by the subject or the like. Therefore, only signals due to the noise floor are likely to generate. In this embodiment, the dark data is obtained with a shutter that is placed in the optical path of the measurement light in the OCT device 1 to block the measurement light.

The CPU 31 acquires the correction parameters for determining the correction value of the OCT data according to depth based on the signal strength of the dark data obtained at S1 (S2). In detail, at S2 of this embodiment, the correction coefficient "a" and the intercept "b", which are examples of the correction parameters, are obtained based on changes in signal strength according to the depth at the data acquisition position of the dark data. Therefore, by acquiring the correction parameters (the correction coefficient and the intercept) based on the dark data, where only signals due to the noise floor are likely to generate, the correction parameters suited to the actually generated noise floor are easily obtained with high accuracy. Also, at S2, the correction parameters (the correction coefficient and the intercept) are acquired based on the OCT data (i.e., the dark data) actually acquired by the OCT device 1 that performs the imaging operation. Therefore, even if the noise floor differs due to device-to-device differences, appropriate correction parameters suited to characteristics of the OCT device can be set.

Here, referring to FIG. 4, one example of a method for setting the correction coefficient based on the dark data will be described. As shown in FIG. 4, in this embodiment, the CPU 31 calculates an approximate line LA of the signal strength according to depths in the dark data. Alternatively, the approximate line LA may be, for example, a regression line obtained by the least squares method. Based on the slope of the obtained approximate line LA, the CPU 31 sets the correction coefficient. Therefore, the set correction coefficient is likely to be an appropriate coefficient according to the status of the noise floor of the dark data that is actually acquired by the OCT device 1.

Returning back to the description with reference to FIG. 3, the CPU 31 sets the correction parameters (the correction coefficient and the intercept) obtained at S2 as the correction parameters corresponding to the scanning rate at the timing of obtaining (capturing) the dark data at S1 and stores the parameters in the NVM 34 (S3). The scanning rate is determined with the scanning speed of the measurement light by the optical scanning unit 14 and the number of interference signals acquired by the light receiving element 22 per unit time. As mentioned above, the new findings indicate that when the number of interference signals acquired per unit time by the light receiving element 22 increases (i.e., shortening the exposure time of the light receiving element 22), both the signal strength of the noise floor and the amount of change in the strength of the noise floor according to depths also increase. Therefore, by setting the correction amount (i.e., the correction parameters) for the OCT data according to the depth corresponding to the scanning rate including the exposure time parameter, the negative effects due to the noise floor can be effectively reduced with higher accuracy.

Next, the CPU 31 determines whether the correction parameter setting process is completed (S4). If not (S4: NO), the scanning rate for acquiring the dark data for next time is changed (S5), and the processes S1 to S4 are repeated. As a result, multiple correction parameters are set according to the scanning rates (i.e., the exposure time of the light receiving element 22). When the correction parameter setting process is completed (S4: YES), the process ends.

As described above, in the first embodiment, based on the OCT data (in this embodiment, the dark data) obtained by the OCT device 1 itself, the correction parameters (i.e., the correction coefficient and the intercept) are set in advance prior to executing the OCT data correction process (see FIG. 5). As described above, the noise floor of the OCT data is less susceptible to influences from the environment such as temperature. Therefore, by determining the correction parameters suited to the OCT device 1 based on the OCT data acquired by itself, there is no need to set the correction parameters every time OCT data is acquired. This makes it easier to reduce the influence by the noise floor via a simple process.

Referring to FIG. 5, the OCT data process in the first embodiment will be described. In this embodiment, the CPU 31 of the OCT device 1 executes the OCT data process shown in FIG. 5 in accordance with the OCT data processing program stored in the NVM 34. First, the CPU 31 determines whether the OCT data (RAW data) to be corrected is acquired (S11). If the RAW data is not acquired (S11: NO), the step of S11 is repeated. When the RAW data is acquired (S11: YES), the CPU 31 identifies the scanning rate (or, alternatively, information related to the exposure time of the light receiving element 22) at the time of acquiring (capturing) the RAW data (S12).

The CPU 31 performs the correction process on the RAW data by subtracting the value obtained by multiplying the correction coefficient "a" by the depth "z" at the data acquisition position from the RAW data (S13). As a result, the influence by the noise floor is reduced appropriately with a simple process. Specifically, at S13, the CPU 31 performs the correction process on the OCT data acquired at S11 based on the correction parameters (the correction coefficient) set according to the scanning rate identified at S12. In other words, depending on the scanning rate at a timing of acquiring the OCT data to be corrected, the CPU 31 changes the correction amount according to the depth. As a result, the influence due to the noise floor, which varies depending on the scanning rate, can be more easily reduced. Additionally, the correction parameters (the correction coefficients) used at step of S13 are preset for the OCT device 1 based on the OCT data (i.e., the dark data) that was acquired by the OCT device 1 itself in the past. Thus, there is no need to set the correction parameters every time the OCT data to be corrected is acquired. At S13, by subtracting the intercept "b" from the RAW data, the influence due to the noise floor is reduced more appropriately.

Based on the corrected OCT data processed at S13, the CPU 31 generates image data (e.g., a two-dimensional tomographic image or a three-dimensional tomographic image) (S14). The image data generated at S14 is high-quality image data with the reduced influence by the noise floor.

The CPU 31 obtains the high-quality image data by inputting the image data generated at S14 into a mathematical model trained by a machine learning algorithm (S15). The mathematical model used at S15 is pre-trained to output high-quality image data where the input image data is improved in quality. Here, if uncorrected image data affected by the noise floor is input into the mathematical model, in many cases, high-quality images with the reduced influence of the noise floor would not be obtained. For example, even when image data is input into the mathematical model, parts of the image that would not appear without the noise floor, such as bright areas, may be included in the image output from the mathematical model. On the other hand, by inputting the corrected image data with less influence by the noise floor into the mathematical model, higher quality image data can be obtained.

The CPU 31 obtains results of at least one of the identified layers shown in the image and the identified boundaries between the layers (hereinafter, referred to as "specific layers/boundaries") by inputting the image data generated at S14 into the mathematical model trained by the machine learning algorithm (S16). The mathematical model used at S16 has been trained to output identification results of the specific layers/boundaries in the input image (in this embodiment, a two-dimensional or three-dimensional tomographic image). Based on the tomographic image data with the reduced influence from the noise floor (i.e., the image data generated at S14), the identification results of the specific layers/boundaries are obtained, thereby making it easier to obtain the highly accurate identification results. Thereafter, the process returns to S11.

It should be noted that the CPU 31 may process at least two pieces of the OCT data obtained at the same position of an organization at different timings. After executing the correction process (S13) based on the depth at the data acquisition position, a motion contrast image (e.g., an OCT angiography image) may be generated based on at least the two pieces of the OCT data. In this case, a high-quality motion contrast image with reduced noise floor effects can be generated.

Alternatively, the CPU 31 may generate Enface image data based on the OCT data subject to the correction process (S13) depending on the depth of the data acquisition position. Enface image data can be, for example, accumulated image data where brightness values are accumulated in the depth direction (i.e., Z-direction) at each position in X-Y direction intersecting the optical axis of the measurement light, accumulated values of spectral data at each position in X-Y direction, brightness data at a certain depth in X-Y direction, or brightness data at any layer of the retina (e.g., the retinal surface layer). In this scenario, a high-quality Enface image with reduced noise floor effects can be generated.

In the first embodiment, the correction parameters are set by the OCT device 1 itself. However, the correction parameters set by another device may be acquired and used by the OCT device 1. Alternatively, based on the OCT data acquired by the OCT device 1, an operator may set the correction parameters (e.g., correction coefficients). The correction parameters set by the operator may be stored in the NVM 34 or the like. Additionally, it is possible to eliminate at least one of the processes of S14 to S16.

Second Embodiment

Figure 6:
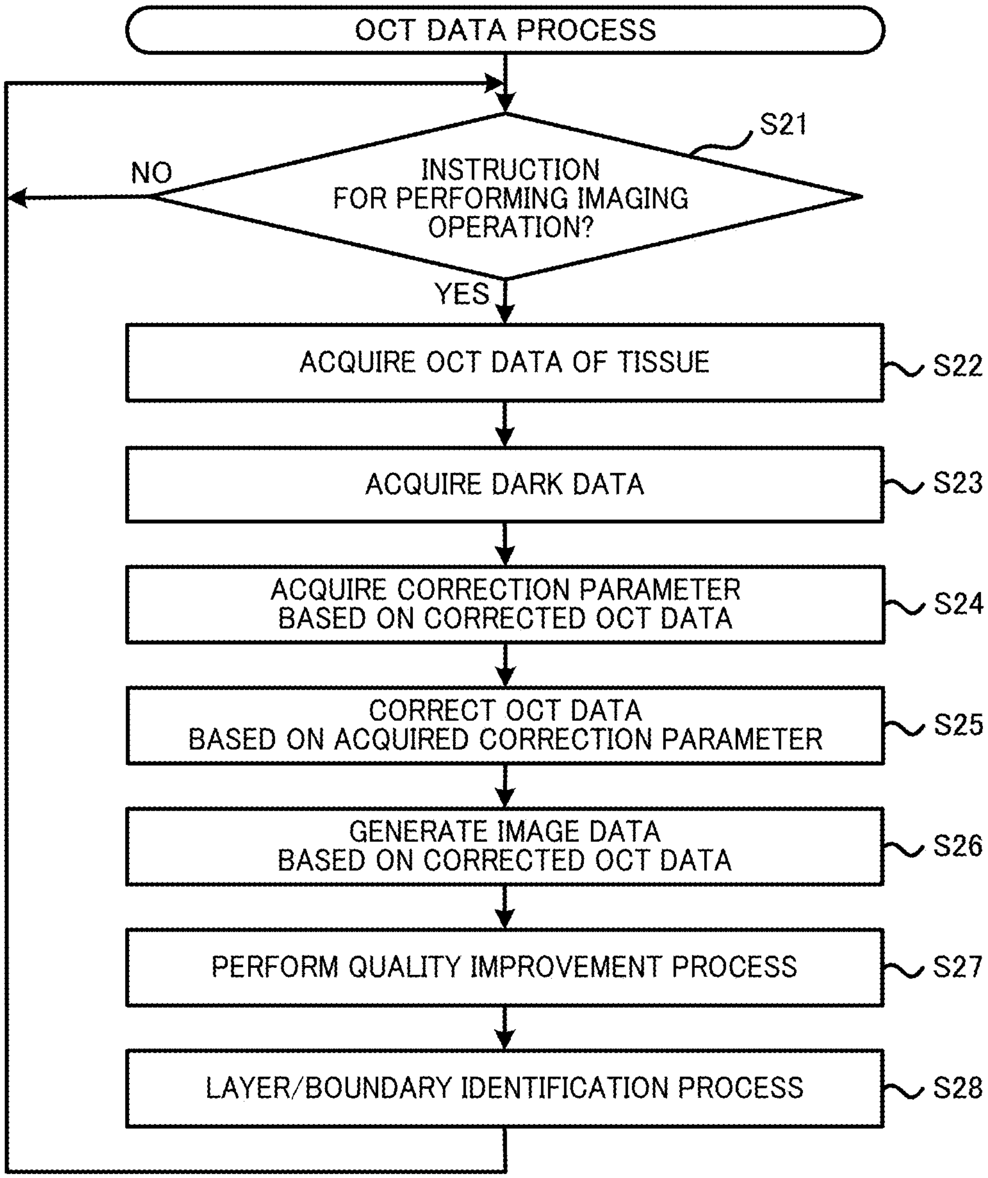
FIG. 6 is flowchart of an OCT data process executed by an OCT device (i.e., an OCT data processing device according to a second embodiment.

Referring to FIG. 6, an OCT data process executed by an OCT device (an OCT data processing device) 1 will be described according to the second embodiment. In the second embodiment, the OCT data processing, every time an operation of capturing (acquiring) target OCT image data (RAW image data) is performed, dark data for setting correction parameters (a correction coefficient and an intercept in this embodiment) is acquired (captured) before and after performing the RAW data imaging operation. A correction process of the RAW data is performed using the correction parameters set based on the dark data. Among steps executed in the second embodiment, steps similar to those described in the first embodiment may be omitted or simplified in the following description.

First, the CPU 31 determines whether an instruction for capturing (imaging) a subject eye's tissue is input (S21). If no instruction is input (S21: NO), the step of S21 is repeated. When the instruction is input (S21: YES), the CPU 31 captures the OCT data (i.e., RAW data) of the subject eye's tissue (S22). Then, the CPU 31 acquires (captures) the dark data at the same scan rate as in the imaging operation at S22 (S23).

The CPU 31 acquires, based on the signal strength of the dark data obtained at S23, correction parameters to determine a correction value for the OCT data according to depth (S24). The process and advantageous effects in S24 are similar to those in S2 of the first embodiment (refer to FIG. 5). Therefore, a detailed description of the process at S24 is omitted.

The CPU 31 performs the correction process on the RAW data acquired at S22 based on the correction parameters obtained at S24 (S25). Specifically, the CPU 31 performs the correction process of the RAW data by multiplying the correction coefficient 'a' obtained at S24 by the depth 'z' at the data acquisition position and subtracting that value from the RAW data according to the depth. Furthermore, the intercept 'b' is subtracted from the RAW data. As described above, the correction parameters used at S25 are set based on the dark data acquired before and after (in this embodiment, immediately after) performing the imaging operation of the RAW data at S22. Therefore, even if the noise floor receives influences from the environment and individual device differences, the noise floor effects are more likely to be reduced appropriately. Furthermore, by setting the correction parameters based on the dark data, the correction parameters suited to the actual noise floor can be set with high accuracy.

Then, the CPU 31 executes an image data generation process based on the corrected OCT data (S26), an image quality improvement process (S27), and a layer/boundary identification process (S28). The steps of S26 to S28 can be the same as S14 to S16 in the first embodiment. At least one of the processes of S26 to S28 may be omitted. Also, as with the first embodiment, the CPU 31 may further execute a motion contrast image generation process and an Enface image generation process.

Third Embodiment

Figure 7:
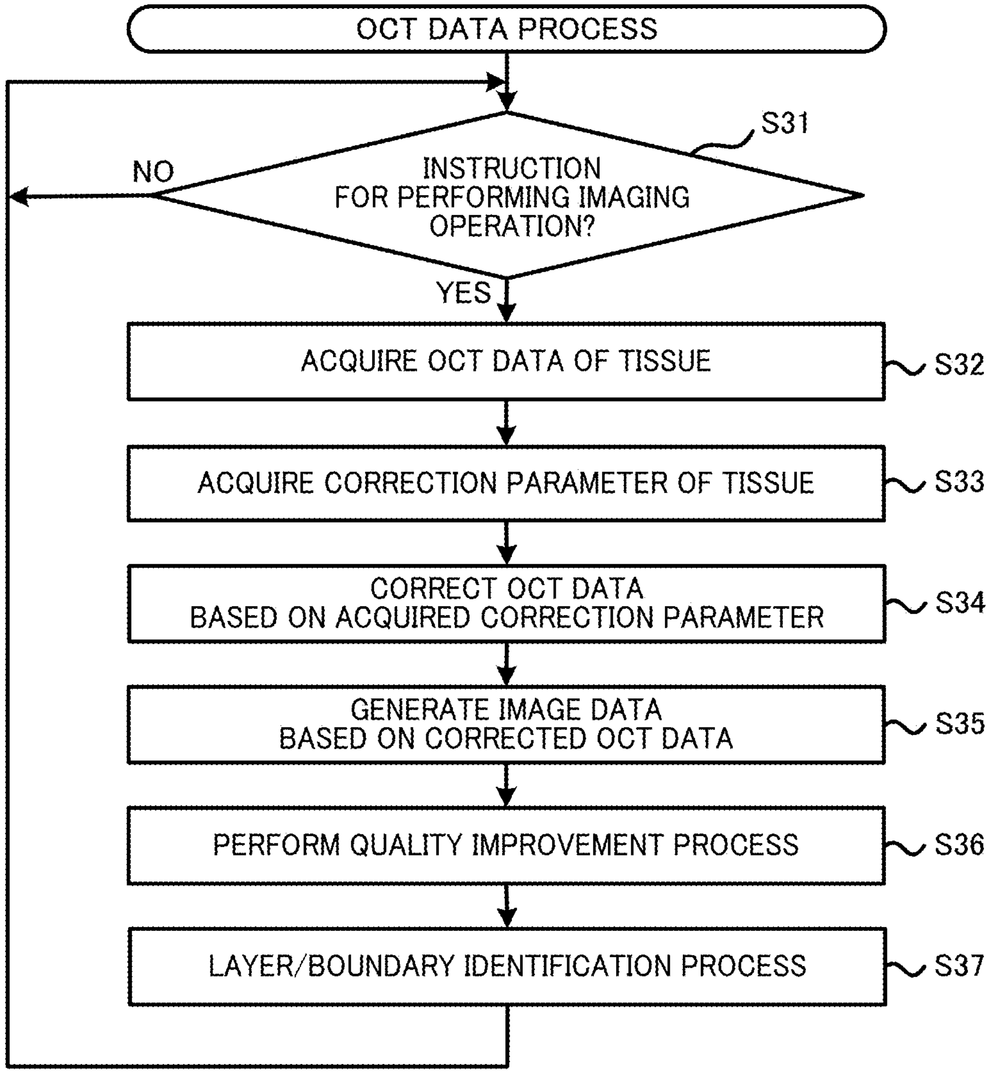
FIG. 7 is a flowchart of an OCT data process executed by an OCT device (i.e., an OCT data processing device) according to a third embodiment.
Figure 8:
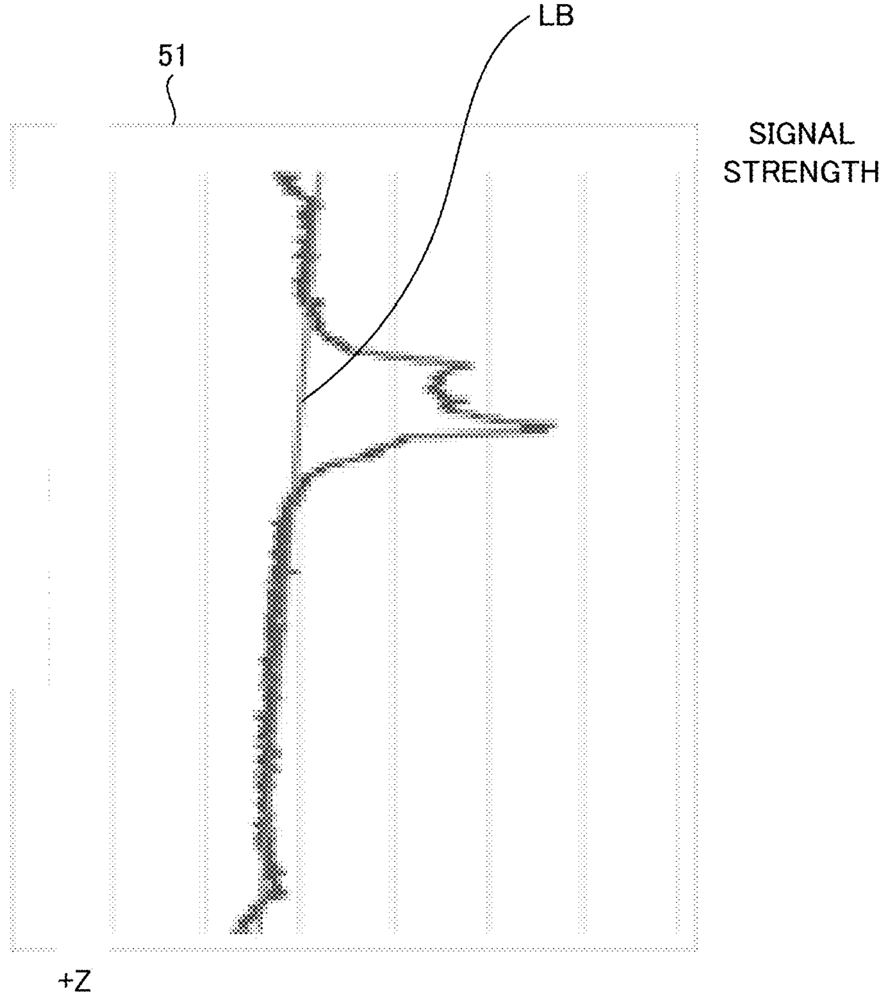
FIG. 8 is a diagram showing a luminance graph of actual OCT data fora tissue and a straight line indicating a slope of a first principal component.

Referring to FIGS. 7 and 8, an OCT data process performed by an OCT device (an OCT data processing device) 1 according to the third embodiment will be described. In the OCT data process of the third embodiment, correction parameters are set based on target OCT data (RAW data) itself, and the RAW data is corrected based on the set correction parameters. Note that for steps executed in the third embodiment that are similar to the steps explained in the first and second embodiments, description may be omitted or simplified.

First, the CPU 31 determines whether an instruction for capturing (imaging) a tissue of the subject eye is input (S31). If not (S31: NO), the determination at S31 is repeated. When the instruction is input (S31: YES), the CPU 31 captures the OCT data (RAW data) of the subject eye's tissue by controlling the light scanning unit 14 and so on (S32).

The CPU 31 obtains, based on the tissue OCT data (RAW data) acquired at S32, correction parameters (a correction coefficient and an intercept) to determine a correction value for the OCT data according to depth (S33). The tissue OCT data acquired at S32, unlike dark data, is captured under a normal condition where incidence of the reflected light of the measurement light onto the light receiving element 22 is allowed. However, it is also possible to set the correction parameters based on the OCT data captured under a normal condition.

Referring to FIG. 8, one example of a method for setting the correction parameters based on the normally captured OCT data will be described. In the luminance graph 51 of FIG. 8, as in FIG. 2, the more it goes downward in the drawing (i.e., goes in +Z-direction), the more the data acquisition position depth increases. Further, the more it goes to the right side in the drawing, the more the signal strength (luminance) increases. In the luminance graph 51 shown in FIG. 8, unlike the luminance graphs 41 shown in FIGS. 2 and 4, there is an area where the signal strength increases (i.e., an area where an image is shown) due to the reflected light of the measurement light caused by the subject (i.e., the imaging target). However, in areas where no image is shown, the signal strength due to the noise floor appear, as in the luminance graphs 41 shown in FIGS. 2 and 4. Therefore, it is possible to set correction parameters (a correction coefficient and an intercept in this embodiment) based on the signal strength in the areas where no image is shown among the OCT data acquired under a normal condition. For instance, in this embodiment, the CPU 31 executes a principal component analysis for the signal strength per depth in the acquired OCT data and sets the correction coefficient based on the slope of the first principal component (for instance, the slope of the straight line LB shown in FIG. 8). As a result, the correction coefficient is set based on the signal strength in the areas where no image is shown.

The CPU 31 executes a correction process on the RAW data obtained at S32 based on the correction parameters obtained at S33 (S34). Specifically, the CPU 31 executes the correction process on the RAW data by obtaining a value by multiplying the depth "z" at the data acquisition position by the correction coefficient "a" obtained at S33. Then, the CPU 31 subtracts the obtained value from the RAW data. Furthermore, the intercept "b" is also subtracted from the RAW data. As described above, the correction parameters used at S34 are set based on the RAW data itself obtained at S32. Therefore, even if the noise floor receives influences from an environment or individual differences in the device, the influence due to the noise floor can be reduced more appropriately.

Next, the CPU 31 performs an image data generation process based on the corrected OCT data (S35), an image quality improvement process (S36), and a layer/boundary identification process (S37). The processes of S35 to S37 can adopt processes similar to those in S14 to S16 of the first embodiment. At least one of the processes of S35 to S37 can be omitted. Additionally, as with the first and second embodiments, the CPU 31 may further execute a motion contrast image generation process and an Enface image generation process.

The technology disclosed in the above embodiments is just one of examples. Therefore, it is possible to modify the technology exemplified in the above embodiments. It is also possible to implement only a part of the multiple technologies exemplified in the above embodiments. For example, processes that change the correction amount of OCT data according to the scanning rate or exposure time can also be omitted.

In the above embodiments, the correction coefficient is used as a correction parameter to determine a correction value for the OCT data according to depth. However, the specific method for OCT data correction process may also be changed. For instance, the CPU 31 may acquire correction amount data, which defines a correction amount for each depth at the data acquisition position, as a correction parameter. The CPU 31 may perform the OCT data correction process by subtracting the correction amount defined for each depth by the correction amount data from the OCT data. In this case, even if the device has a noise floor not proportional to depth, the influence by the noise floor is appropriately reduced. The method for setting correction amount data may be chosen as appropriate. For instance, in S2 of FIG. 3 and S24 of FIG. 6, the CPU 31 may set signal strength per depth in the dark data acquired at S1 or S23 as the correction amount data to be subtracted from the OCT data for each depth.

The invention claimed is:

1. A method comprising:

acquiring OCT data of a tissue of a subject eye in a depth direction that is generated by processing an interference signal generated from measurement light reflected by the tissue and reference light that are split by a light splitting element;

performing a correction process to reduce an effect by a noise floor in the OCT data using a plurality of correction amounts each of which is set in accordance with depth at a corresponding data acquisition position, wherein strength of the noise floor varies depending on the depth;

generating an image data of the tissue based on the OCT data on which the correction process was performed in accordance with the depth at the corresponding data acquisition position; and acquiring a high-quality image data by inputting the image data into a mathematical model that has been trained by a machine learning algorithm to output improved-quality image data from input image data.

2. An OCT device comprising:

an OCT light source;

a light splitting element that is configured to split light emitted from the OCT light source into measurement light and reference light;

an optical system that is configured to guide the measurement light split by the splitting light element toward a tissue of a subject eye;

a light receiving element that is configured to detect an interference signal generated from the measurement light reflected by the tissue and the reference light split by the light splitting element; and a controller configured to:

acquire OCT data of the tissue in a depth direction that is generated by processing the interference signal detected by the light receiving element; and perform a correction process to reduce an effect by a noise floor in the OCT data using a plurality of correction amounts each of which is set in accordance with depth at a corresponding data acquisition position, wherein strength of the noise floor varies depending on the depth of the corresponding data acquisition position.

3. The OCT device according to claim 2, wherein the controller is further configured to perform the correction process using, as each of the correction amounts, a value that is acquired by multiplying a correction coefficient in accordance with a variation amount of the noise floor per unit variation amount of the depth at the corresponding data acquisition position by the depth of the corresponding data acquisition position.

4. The OCT device according to claim 2, wherein a correction parameter to calculate the correction amounts is particularly set for the OCT device based on a variation amount of signal strength in accordance with the depth at the corresponding data acquisition position in the OCT data that is acquired by the OCT device by performing an imaging operation.

5. The OCT device according to claim 4, wherein the correction parameter has been particularly set for the OCT device in advance based on data that was previously acquired by the OCT device by performing the imaging operation.

6. The OCT device according to claim 4, wherein the controller is further configured to set the correction parameter based on (i) the OCT data that is a correction target and acquired every time the imaging operation is performed or (ii) the OCT data acquired before or after performing the imagine operation.

7. The OCT device according to claim 4, wherein the correction parameter is set based on variation amounts of signal strength of dark data in accordance with the depth at the corresponding data acquisition position, and a signal increase due to a reflected light of the measurement light does not occur in the dark data.

8. The OCT device according to claim 2, wherein the controller is further configured to change each of the correction amounts in accordance with a number of interference signals acquired per unit time by the light receiving element when the OCT data is acquired.

9. The OCT device according to claim 2, wherein the controller is further configured to:

generate image data of the tissue based on the OCT data on which the correction process was performed in accordance with the depth at the corresponding data acquisition position; and acquire a high-quality image data by inputting the image data into a mathematical model that has been trained by a machine learning algorithm to output improved-quality image data from input image data.

10. A non-transitory, computer readable, storage medium storing an OCT data processing program that is executed by a controller of an OCT data processing device that is configured to process data acquired by an OCT device, the program, when executed by the controller, causing the controller to perform:

acquiring OCT data of a tissue of a subject eye in a depth direction that is generated by processing an interference signal generated from measurement light reflected by the tissue and reference light that are split by a light splitting element; and performing a correction process to reduce an effect by a noise floor in the OCT data using a plurality of correction amounts each of which is set in accordance with depth at a corresponding data acquisition position, wherein strength of the noise floor varies depending on the depth at the corresponding data acquisition position.

11. The storage medium according to claim 10, wherein the program further causes the controller to perform:

generating an image data of the tissue based on the OCT data on which the correction process was performed in accordance with the depth at the corresponding data acquisition position; and acquiring a high-quality image data by inputting the image data into a mathematical model that has been trained by a machine learning algorithm to output improved-quality image data from input image data.

* * * * *